(12) United States Patent
Bieglmayer et al.

(10) Patent No.: US 9,395,355 B2
(45) Date of Patent: Jul. 19, 2016

(54) ASSESSMENT OF PHYSIOLOGICAL CONDITIONS

(75) Inventors: Christian Bieglmayer, Vienna (AT); Stefan Kudlacek, Vienna (AT)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 347 days.

(21) Appl. No.: 12/824,308

(22) Filed: Jun. 28, 2010

(65) Prior Publication Data
US 2010/0311095 A1    Dec. 9, 2010

Related U.S. Application Data

(63) Continuation of application No. PCT/EP2007/011462, filed on Dec. 28, 2007.

(51) Int. Cl.
G06F 19/10 (2011.01)
G06F 19/24 (2011.01)
G06F 19/26 (2011.01)
G01N 33/50 (2006.01)
G06F 19/18 (2011.01)

(52) U.S. Cl.
CPC ........ *G01N 33/5091* (2013.01); *G01N 2333/51* (2013.01); *G01N 2333/78* (2013.01); *G01N 2333/916* (2013.01); *G06F 19/18* (2013.01)

(58) Field of Classification Search
None
See application file for complete search history.

(56) References Cited

FOREIGN PATENT DOCUMENTS

| JP | 2004-501-348 A | 1/2004 |
|---|---|---|
| JP | 2007-522-457 A | 8/2007 |
| JP | 2007-523-209 A | 8/2007 |
| WO | 96/12187 A1 | 4/1996 |
| WO | 00/13024 A1 | 3/2000 |
| WO | 00/22437 A1 | 4/2000 |
| WO | 01/22093 A1 | 3/2001 |
| WO | 02/96284 A1 | 12/2002 |
| WO | 2004/059293 A3 | 7/2004 |
| WO | 2006/045593 A1 | 5/2006 |
| WO | 2007/092433 A3 | 8/2007 |

OTHER PUBLICATIONS

James et al. Mathematics Dictionary D. Van Nostrand Co. Inc. Princeton pp. 317and 414-415 (1959).*
Cuckle et al. Estimating a woman's risk of having a pregnancy associated with Down's syndrome using her age and serum alpha-fetoprotein level. British Journal of Obstetrics and Gynecology vol. 94, pp. 387-402 (1987).*
Hawmi et al. Markers of Bone Turnover in Postmenopausal Women Receiveing Hormone Replacement Therapy. Clinical Chemistry and Laboratory Medicine vol. 39, pp. 414-417 (2001).*
Panichi et al. C-Reactive Protein and Interleukin-6 Levels are Related to Renal Function in Predialytic Chronic Renal Failure. Nephron vol. 91 pp. 594-600 (2002).*
Translation of Office Action dated Nov. 15, 2011 for Corresponding Japanese Application No. 2010-540032.
Bauer, Douglas C. et al., "Biochemical Markers of Bone Turnover and Prediction of Hip Bone Loss in Older Women: The Study of Osteoporotic Fractures," Journal of Bone and Mineral Research, 1999, pp. 1404-1410, vol. 14, No. 8.
Bieglmayer, Christian et al., "Parathyroid Hormone Monitoring during Total Parathyroidectomy for Renal Hyperparathyroidism: Pilot Study of the Impact of Renal Function and Assay Specificity," Clinical Chemistry, 2006, pp. 1112-1119, vol. 52, No. 6.
Bonde, Martin et al., "Immunoassay for Quantifying Type I Collagen Degradation Products in Urine Evaluated," Clinical Chemistry, 1994, pp. 2022-2025, vol. 40, No. 11.
Bruyere, Olivier et al., "Interest of biochemical markers of bone turnover for long-term prediction of new vertebral fracture in postmenopausal osteoporotic women," Maturitas, 2003, pp. 259-265, vol. 44.
Chapurlat, R. D. et al., "Serum Type I Collagen Breakdown Product (Serum CTX) Predicts Hip Fracture Risk in Elderly Women: The EPIDOS Study," Bone, Aug. 2000, pp. 283-286, vol. 27, No. 2.
Chesnut, Charles H., III et al., "Hormone Replacement Therapy in Postmenopausal Women: Urinary N-Telopeptide of Type I Collagen Monitors Therapeutic Effect and Predicts Response of Bone Mineral Density," American Journal of Medicine, 1997, pp. 29-37, vol. 102.
Christenson, Robert H., "Biochemical Markers of Bone Metabolism: An Overview," Clinical Biochemistry, 1997, pp. 573-593, vol. 30, No. 8.
Christgau, S. et al., "Serum CrossLaps for Monitoring the Response in Individuals Undergoing Antiresorptive Therapy," Bone, May 2000, pp. 505-511, vol. 26, No. 5.
Christiansen C. et al., "Dose dependent effects on bone resorption and formation of intermittently administered intravenous ibandronate," Osteoporosis International, Jul. 2003, pp. 609-613, vol. 14, No. 7.
Delmas, P. D. et al., "The Use of Biochemical Markers of Bone Turnover in Osteoporosis," Osteoporosis International, 2000, pp. S2-17, Supplement 6.
Dobnig, Harald et al., "Early Changes in Biochemical Markers of Bone Formation Correlate with Improvements in Bone Structure during Teriparatide Therapy," The Journal of Clinical Endocrinology & Metabolism, 2005, pp. 3970-3977, vol. 90, No. 7.
Exner, Markus et al., "Myeloperosidase Predicts Progression of Carotid Stenosis in States of Low High=Density Lipoprotein Cholesterol," Journal of the American College of Cardiology, 2006, pp. 2212-2218, vol. 47, No. 11.
Garnero, Patrick. and Delmas, Pierre D., "Biochemical Markers of Bone Turnover," Endocrinology and Metabolism Clinics of North America, Jun. 1998, pp. 303-323, vol. 27, No. 2.

(Continued)

*Primary Examiner* — John S Brusca
(74) *Attorney, Agent, or Firm* — Dinsmore & Shohl LLP (57) ABSTRACT

The present invention relates to a method for assessing in vitro the balance and the overall dynamics of a physiological condition, wherein a) a first biochemical marker representing a first biochemical process associated with the physiological condition is measured, b) a second biochemical marker representing a second biochemical process associated with the physiological condition is measured, c) the ratio of the results obtained in (a) and (b) is calculated, d) the square root of the sum of the squared results obtained in (a) and (b) is calculated and, e) wherein the ratio calculated in (c) is used to assess the balance of the physiological condition and wherein the square root calculated in (d) is used to assess the overall dynamics of the physiological condition.

10 Claims, 6 Drawing Sheets

(56) References Cited

OTHER PUBLICATIONS

Garnero, P. et al., "Markers of Bone Resorption Predict Hip Fracture in Elderly Women: The EPIDOS Prospective Study," Journal of Bone and Mineral Research, 1996, pp. 1531-1538, vol. 11, No. 10.

Garnero, Patrick et al., "Biochemical Markers of Bone Turnover, Endogenous Hormones and the Risk of Fractures in Postmenopausal Women: The OFELY Study," Journal of Bone and Mineral Research, 2000, pp. 1526-1536, vol. 15, No. 8.

Garnero, Patrick et al., "Comparison of New Biochemical Markers of Bone Turnover in Late Postmenopausal Osteoporotic Women in Response to Alendronate Treatment," Journal of Clinical Endocrinology and Metabolism, 1994, pp. 1693-1700, vol. 79, No. 6.

Garnero, Patrick et al., "Long-Term Variability of Markers of Bone Turnover in Postmenopausal Women and Implications for Their Clinical Use: The OFELY Study," Journal of Bone and Mineral Research, 2003, pp. 1789-1794, vol. 18, No. 10.

Garnero, Patrick et al., "Markers of Bone Turnover Predict Postmenopausal Forearm Bone Loss Over 4 Years: The OFELY Study," Journal of Bone and Mineral Research, 1999, pp. 1614-1621, vol. 14, No. 9.

Gerdhem, Paul et al., "Biochemical Markers of Bone Metabolism and Prediction of Fracture in Elderly Women," Journal of Bone and Mineral Research, 2004, pp. 386-393, vol. 19, No. 3.

Greenspan, Susan L. et al., "Early Changes in Serum N-Telopeptide and C-Telopeptide Cross-Linked Collagen Type 1 Predict Long-Term Response to Alendronate Therapy in Elderly Women," The Journal of Clinical Endocrinology & Metabolism, 2000, pp. 3537-3540, vol. 85, No. 10.

Gundberg, Caren M., "Biochemical Markers of Bone Formation," Clinics in Laboratory Medicine, Sep. 2000, pp. 489-501, vol. 20, No. 3.

Hannon, Rosemary A. and Eastell, Richard, Journal of the British Menopause Society, Mar. 2003, pp. 10-15, vol. 9.

Iki, Masayuki et al., "Biochemical markers of bone turnover may predict progression to osteoporosis in osteopenic women: the JPOS Cohort Study," Journal of Bone and Mineral Metabolism, 2007, pp. 122-129, vol. 25.

Iki, M. et al., "Biochemical markers of bone turnover predict bone loss in perimenopausal women but not in postmenopausal women—the Japanese Population-based Osteoporosis (JPOS) Cohort Study," Osteoporos International, 2006, pp. 1086-1095, vol. 17.

Jukema, J. Wouter et al., "LDL-C/HDL-C ratio in subjects with cardiovascular disease and a low HDL-C: results of the RADAR (Rosuvastatin and Atorvastatin in different Dosages and Reverse cholesterol transport) study," Current Medical Research and Opinions, 2005, pp. 1865-1874, vol. 21, No. 11.

Kanis, J. A. et al., "Risk of Hip Fracture According to the World Health Organization Criteria for Osteopenia and Osteoporosis," Bone, Nov. 2000, pp. 585-590, vol. 27, No. 5.

Kim, Sang Wan et al., "Early Changes in Biochemical Markers of Bone Turnover Predict Bone Mineral Density Response to Antiresorptive Therapy in Korean Postmenopausal Women with Osteoporosis," Endocrine Journal, 2005, pp. 667-674, vol. 52, No. 6.

Kronborg, J. et al., "Proinsulin:insulin and insulin:glucose ratios as predictors of carotid plaque growth: a population-based 7 year follow-up of the Tromso Study," Diabetologia, 2007, pp. 1607-1614, vol. 50.

Kudlacek, S. et al., "Assessment of vitamin D and calcium status in healthy adult Austrians," European Journal of Clinical Investigation, 2003, pp. 323-331, vol. 33, No. 4.

Kudlacek, S. et al., "Normative data of bone mineral density in an unselected adult Austrian population," European Journal of Clinical Investigation, 2003, pp. 332-339, vol. 33, No. 4.

Lenora, J. et al., "Prediction of bone loss using biochemical markers of bone turnover," Osteoporos International, 2007, pp. 1297-1305, vol. 18.

Levine, Richard J. et al., "Soluble Endoglin and Other Circulating Antiangiogenic Factors in Preeclampsia," The New England Journal of Medicine, Sep. 7, 2006, pp. 992-1005, vol. 355, No. 10.

Meier, Christian et al., "Bone Resorption and Osteoporotic Fractures in Elderly Men: The Dubbo Osteoporosis Epidemiology Study," Journal of Bone and Mineral Research, 2005, pp. 579-587, vol. 20, No. 4.

Meier, Christian et al., "Endocrine regulation of bone turnover in men," Clinical Endocrinology, 2005, pp. 603-616, vol. 63.

Raisz, L. et al., "Short-Term Risedronate Treatment in Postmenopausal Women: Effects on Biochemical Markers of Bone Turnover," Osteoporosis International, 2000, pp. 615-620, vol. 11.

Ross, Philip D., "Predicting Bone Loss and Fracture Risk with Biochemical Markers," Journal of Clinical Densitometry, Fall 1999, pp. 285-294, vol. 2, No. 3.

Seibel, M. J., "Biochemical markers of bone metabolism in the assessment of osteoporosis: Useful or not?," Journal of Endocrinological Investigation, 2003, pp. 464-471, No. 26.

Seibel, Markus J., "Biochemical markers of bone remodeling," Endocrinology and Metabolism Clinics of North America, 2003, pp. 83-113, No. 32.

Srivastava, Apurva K. et al., "Clinical use of serum and urine bone markers in the management of osteoporosis," Current Medical Research and Opinions, 2005, pp. 1015-1026, vol. 21, No. 7.

Stepan, J. J., "Clinical utility of bone markers in the evaluation and follow-up of osteoporotic patients: Why are the markers poorly accepted by clinicians?" Journal of Endocrinological Investigation, 2003, pp. 458-463, vol. 26.

Takahara, Kenji et al., "Change of cross-linked telopeptide of type I collagen (ICTP) and other bone resorption markers in patients with bone fragility fractures," Journal of Orthopaedic Science, 2007, pp. 219-226, vol. 12.

Thadhani, Ravi et al., "First Trimester Placental Growth Factor and Soluble Fms-Like Tyrosine Kinase 1 and Risk for Preeclampsia," The Journal of Clinical Endocrinology & Metabolism, 2004, pp. 770-775, vol. 89, No. 2.

Vermeulen, Alex et al., "A Critical Evaluation of Simple Methods for the Estimation of Free Testosterone in Serum," The Journal of Clinical Endocrinology & Metabolism, 1999, pp. 3666-3672, vol. 84, No. 10.

Young, William F., Jr., "Minireview: Primary Aldosteronism—Changing Concepts in Diagnosis and Treatment," Endocrinology, 2003, pp. 2208-2213, vol. 144, No. 6.

Van Daele, Paulus L. A. et al., "Case-control analysis of bone resorption markers, disability and hip fracture risk: the Rotterdam study," British Medical Journal, 1996, pp. 482-483, vol. 312.

\* cited by examiner

ASSESSMENT OF PHYSIOLOGICAL CONDITIONS

TECHNICAL FIELD

The present invention relates to a method for assessing the balance and the overall dynamics of a physiological condition.

BACKGROUND

Physiological conditions frequently involve several different counter-acting and balanced biochemical processes. Under pathological conditions the dynamics and/or the balance of such usually balanced physiological process is/are no longer given. Thus, in the assessment of a physiological condition, it might be desirable to provide a correlation of these different counter-acting biochemical processes to this physiological condition. This might be particularly useful in classifying or grouping of individuals, in the assessment of physiological and pathological conditions, in the monitoring of the efficacy of therapeutic regimens, in the scientific presentation of complex coherences, etc.

An example of a physiological condition that is based on counter-acting physiological processes and under normal circumstances is well-balanced is bone metabolism. The dynamic manner of bone remodeling results from two counter-acting and balanced processes: bone formation and bone resorption. To quite some extend these processes are reflected by biochemical markers of bone turnover, which can be measured in plasma, serum and urine. Characteristics of bone markers as well as their clinical use have been extensively reviewed (Christenson, Clin Biochem 30 (1997), 573-593; Garnero & Delmas, Endocrinol Metab Clin North Am 27 (1998), 303-323; Delmas et al., Osteoporos Int 11 (Suppl. 6) (2000), S2-17; Seibel, Endocrinol Metab Clin North Am 32 (2003), 83-113), Seibel, J Endocrinol Invest 26 (2003), 464-471; Meier et al., Clin Endocr 63 (2005), 603-616). For clinical purposes a distinction is made between markers of bone formation and markers of bone resorption. In postmenopausal women, high bone turnover, often is associated with a significantly increased loss in bone mass as compared to the bone loss for women having a normal or low bone turnover. High, normal, or low bone turnover usually are paralleled by increased levels of bone markers, normal levels of bone markers or lower than normal levels of bone markers, respectively (Garnero et al., J Bone Miner Res 14 (1999), 1614-1621; Srivastava et al., Curr Med Res Opin 21 (2005), 1015-1026). High concentrations of bone turnover markers were associated with an increased bone loss in the hip, spine and femoral neck compared with low levels (Chesnut et al., Am J Med 102 (1997), 29-37, Bauer et al., J Bone Miner Res 14 (1999), 1404-1410; Iki et al., Osteoporos Int 17 (2006), 1086-1095; Lenora et al., Osteoporos Int 18 (2007), 1297-1305). The classification of women having elevated bone turnover by levels of resorption and formation markers remained rather stable over 4 years. Elevated turnover may predict progression to osteoporosis in osteopenic women (Garnero et al., J Bone Min Res 18 (2003), 1789-1794; Iki et al., J Bone Miner Metab 25 (2007), 122-129).

Importantly, elevated bone markers are an independent risk factor for fractures, additive to bone mineral density (BMD) (Garnero et al, J Bone Miner Res 11 (1996), 1531-1538; van Daele et al., Brit Med J 312 (1996), 482-483; Ross, J Clin Densitometry 2 (1999), 285-294; Garnero et al., J Bone Miner Res 15 (2000), 1526-1536; Chapurlat et al., Bone 27 (2000), 283-286; Hannon & Eastell, J Brit Menopaus Soc 9 (2003), 10-15; Bruyere et al., Maturitas 44 (2003), 259-265; Gerdhem et al., J Bone Mineral Res 19 (2004), 386-393; Meier et al., J Bone Miner Res 20 (2005), 579-587). This was observed especially with resorption markers. Relating the concentrations of formation markers to fracture risk has given conflicting findings (Gerdhem et al. (2004), supra; Gundberg, Clin Lab Med 20 (2000), 489-501).

The main interest in bone markers results from the failure of BMD measurement in monitoring the efficacy of treatment against osteoporosis in the individual patient (Stepan, J Endocrinol Invest 26 (2003), 458-463). Changes in BMD due to anti-resorptive or anabolic medications are rather small and become detectable only after at least 1 to 2 years of treatment. However, in clinical practice it is desirable to detect effectiveness of treatment within a few months. An early prediction of BMD response by bone markers became evident from intervention studies with hormone replacement therapy and bisphoshonates (Chesnut et al. (1997), supra; (Garnero et al., J Clin Endocr Metab 79 (1994), 1693-1700; Christgau et al., Bone 26 (2000), 505-511; Greenspan et al., J Clin Endocr Metab 85 (2000), 3537-3540; Christiansen et al., Osteoporos Int 14 (2003), 609-613; Raisz et al., Osteoporos Int 11 (2000), 615-620). While type I collagen derived resorption markers showed a fast response at the latest within 3 to 6 month of anti resorptive therapy, a somewhat delayed decrease in concentrations was observed with formation markers (Garnero et al. (1994), supra; Christiansen et al. (2003), supra; Raisz et al. (2000), supra). In therapy responders both marker types finally declined to normal premenopausal ranges, indicating a normalization of bone turnover. A disturbed balance between markers of bone formation and markers of bone resorption was also observed in anabolic therapy regimens by Teripatide (Dobnig et al., J Clin Endocrinol Metab 90 (2005), 3970-3977).

There is strong evidence from intervention studies that a surveillance of therapy in osteoporotic patients by bone markers is helpful to select early responders and non-responders. However, the interpretation of bone marker data is somewhat cumbersome. The marker concentrations have to be considered in relation to age and gender specific reference ranges and in connection to previous medical reports. In place of the numeric concentration results of the biomarkers, it would be preferable to gain a direct insight into the balance and rate of bone turnover, which are the leading factors to estimate fracture risk, dynamics of bone turnover and prognosis.

WO 96/12187 discloses a diagnostic method wherein the concentration of a set of biomarkers known to be associated with the disease is measured, the digitized values of the biomarker concentrations are scaled and the scaled values are introduced to a trained neural network, wherein the output values from the neural network tend toward the upper value in the presence of the disease and the output values tend toward the lower value, when the disease is absent.

WO 00/13024 refers to a method of predicting or diagnosing a skeletal disorder, wherein the level of at least one regulator or marker of bone remodeling is measured or estimated in the sample. The level is compared with a standard in order to determine whether the level of the regulator or marker falls within a range indicative of a potential to progress to exhibit overt symptoms of the skeletal disorder. For example, the method may comprise measuring a bone resorption marker and a bone formation marker and determining the ratio of both markers.

WO 00/22437 refers to a method for predicting a treatment response and compliance of an individual after an anti-resorptive therapy, wherein the base line of a bone marker at the beginning of the anti-resorptive therapy is measured, a level of the bone marker after a first predetermined time period of anti-responsive therapy is measured and a probability of response in bone mass is generated after a second predetermined time period of the anti-resorptive therapy from a change of the bone marker level from a base line and the level of bone marker at either the base line or at the first predetermined time.

WO 01/22093 refers to a method for monitoring an effect of administration of a parathyroid hormone to a subject wherein a level of an enzyme indicative of an osteoblastic process of bone formation, a product of collagen biosynthesis, a product of collagen degradation or a combination thereof is measured and the level determined is correlated with an effect of administration of a parathyroid hormone.

WO 02/096284 refers to a method for diagnosis of bone disease wherein a mathematical function is used to relate the level of one or more biomarkers with a numerical value relating to one or more imaging descriptors comprising predetermined features from images defining bone disease characteristics to obtain a test value. The test value is compared with a control value, wherein a test value which differs from the control value by a predetermined amount is indicative of bone disease. The mathematical function may be selected from divisions, products, sums, logarithmic functions, exponential functions or combinations thereof.

WO 2004/059293 refers to a method of symptom-based diagnosis, wherein a test sample is analyzed for the presence or amount of a plurality of markers which are selected to identify the presence or absence of conditions within the differential diagnosis of a symptom. The presence or amount of markers in the test sample is correlated to the presence or absence of a condition.

WO 2007/092433 refers to a method with a predetermined level of predictability for assessing a risk of development of osteoporosis, pre-osteoporosis or bone fracture, wherein the level of one or more osteoporosis risk markers is measured and a clinically significant alteration in the level of the markers is measured, wherein the alteration indicates an increased risk of developing osteoporosis, pre-osteoporosis or bone fracture.

None of the above-identified methods, however, describes a method which is capable of assessing both, the balance and the overall dynamics of a physiological condition.

Hamwi et al. (Clin. Chem. Lab. Med 39 (2001), 414-417) describe the effects of hormone replacement therapy on biochemical markers of bone turnover. The overall bone turnover is expressed as area-product of the level of a bone formation marker and a bone resorption marker. Further, the resorption/formation ratio is determined. The results, however, are considered as preliminary and it is indicated that the clinical suitability of the marker ratio and area plot will have to be further tested.

SUMMARY

A subject-matter of the present invention is a method for assessing in vitro the balance and the overall dynamics of a physiological condition, wherein a) a first biochemical marker representing a first biochemical process associated with the physiological condition is measured, b) a second biochemical marker representing a second biochemical process associated with the physiological condition is measured, c) the ratio of the results obtained in (a) and (b) is calculated, and d) the square root of the sum of the squared results obtained in (a) and (b) is calculated, e) wherein the ratio calculated in (c) is used to assess the balance of the physiological condition and wherein the square root calculated in (d) is used to assess the overall dynamics of the physiological condition.

The method of the present invention is suitable for the assessment of both the balance and the overall dynamics of a physiological condition. The term "balance" refers to the status of the physiological condition as a result of at least two biochemical processes, e.g. complementary and/or counter-acting biochemical processes. The balance may be a fluctuating balance depending on alterations in the biological processes. According to the present invention, the balance of the physiological condition is determined by calculating the ratio of test results obtained from determining a first biochemical marker and a second biochemical marker. The term "overall dynamics" refers to the magnitude of the status of the physiological condition. The overall dynamics is determined by calculating the square root of the sum of the squared results for determining the first and second biochemical marker.

The combined determination of balance and overall dynamics (magnitude) allows for an accurate assessment of the physiological condition.

The physiological condition is a condition, which is the result of at least two biochemical processes, e.g. complementary and/or counter-acting biochemical processes, which are related to different biochemical markers and can be ascertained by measurement of such markers. Specific examples of physiological conditions are e.g. bone metabolism, lipid/cholesterol metabolism, carotid plaque growth, preeclampsia, androgenicity/testosterone level, thyroid function, primary aldosteronism, etc.

In one embodiment the physiological condition is bone metabolism. Bone metabolism involves a fluctuating balance between two counter-acting biochemical processes, namely bone formation and bone resorption. Thus, in a preferred embodiment of the present invention, the first biochemical marker is a marker of bone formation and the second biochemical marker is a marker of bone resorption. Preferred markers of bone formation are e.g. bone alkaline phosphatase, osteocalcin (OC) as well as physiologically occurring fragments or secondary modifications thereof and aminoterminal peptide of type I collagen (P1NP). The N-terminal as well as the C-terminal pro-peptide of type I collagen (P1NP and P1CP), respectively, are clipped from the precursor procollagen during or shortly after polypeptide synthesis and therefore are considered to be markers of bone formation. Specific examples for markers of bone resorption are the cleavage products of type I collagen, such as cross-linked telopeptides from the C- or N-terminus, e.g. cross-linked N-telopeptide of type I collagen (NTX), cross-linked C-telopeptide of type I collagen (CTX), also known as β-Cross-Laps® (Bonde, M., et al., Clin. Chem. 40 (1994) 2022-2025), type I collagen carboxyterminal telopeptide (ICTP) referring to a fragment which originally has been derived from cyanobromide cleavage, or non-collagen markers like tartrate-resistant acidic phosphatase. Preferably, the marker of bone formation is OC and/or P1NP. Preferably, the marker of bone resorption is CTX.

A further example for a physiological condition that is based on counter-acting biochemical processes is found in lipid metabolism. The determination of the cholesterol level is very important, because it is associated with the risk of ischemic heart disease. However, the absolute level of cholesterol alone may not suffice to assess a future cardiac risk. Rather it may be important to individually analyze both the so-called good cholesterol (HDL, high density lipoprotein) as well as the so-called bad cholesterol (LDL, low density lipoprotein). It may be even more important and provide more insight into lipid metabolism if the method according to the present invention is used. In this method a first biochemical marker representing a first biochemical process may e.g. be the LDL-cholesterol level (a marker for a high risk of heart disease and responsible for transporting cholesterol to the cells) and a second biochemical marker representing a second biochemical process may be the HDL-cholesterol level (a marker for a low risk of heart disease, responsible for transport of cholesterol away from the cells). Thus, the first biochemical marker may be the LDL-cholesterol level and the second biochemical marker may be the HDL-cholesterol level (Jukema et al., Curr. Med. Res. Opin. 21 (2005), 1865-1874).

In a further embodiment, the present invention relates to the physiological condition of carotid plaque growth. It is known that in the assessment of carotid plaque growth several markers or marker ratios like the proinsulin: insulin ratio or the insulin:glucose ratio (Kronborg et al., Diabetologia (2007) 50:1607-1614) may be helpful. According to the present invention balance as well as magnitude of these markers of carbohydrate metabolism, namely proinsulin and insulin or insulin and glucose can be apprehended.

A further physiological condition to which the method according to this invention may be applied is preeclampsia. In the assessment of balance and overall dynamics of preeclampsia, a first biochemical marker may be placental growth factor and a second marker may be an inhibitor of placental growth factor, like Fms-like tyrosine kinase 1 (Thadhani et al., J. Clin. Endocrin. Metab. (2004) 89:770-775) or soluble endoglin (Levine et al., New Engl. J. Med. (2006), 55:992-1005.

In a further embodiment the present invention relates to androgenicity as a physiological condition. In the determination of the testosterone status different methods provide different kinds of insight into the fraction of bioactive testosterone of an individual, like the measurement or a calculation of free testosterone, determination of bio-available testosterone or use of the free androgen index (Vermeulen et al, J. Clin. Endocrin. Metab. (1999), 3666-3672). In one embodiment further insight can be obtained by processing concentrations of testosterone and of sex hormone binding globulin (SHBG) as physiological counterparts according to the present invention as the first and the second biochemical marker. Testosterone is transported in the circulation tightly bound to SHBG, and apparently only the non-SHBG-bound fraction is responsible for bio-activity. Balance together with magnitude of the complementary parameters testosterone and SHBG will primarily define the androgen status.

A further example for a physiological condition that is based on counter-acting biochemical processes is found in the assessment of thyroid function. In the determination of thyroid function, TSH (thyroid stimulating hormone) and FT4 (free T4) are important feed back controlled parameters, which are preferably used to exclude or to diagnose a hypothyroid or hyperthyroid function. The present invention can be applied in monitoring the efficacy of therapeutic strategies in an individual patient, by using TSH as the first and FT4 as the second biochemical parameter.

In a further embodiment of the present invention relates to the diagnosis of hyperparathyroidism, a disease characterized by a disturbed calcium homeostasis by an impaired counter-balance of parathyroid hormone (PTH) and calcium ions (Ca). Diagnosis may be embroiled by the fact, that PTH and Ca levels both in the upper reference range may be even indicative (Bieglmayer et al., Clin. Chem. (2006), 52:112-1119). From a representative reference group the PTH and Ca concentrations may serve as first and second biochemical markers, respectively, which are transmuted according to the present investigation. Patient's data outside the reference distribution can indicate the disease.

Yet a further example for a physiological condition that is based on counter-acting biochemical processes is primary aldosteronism. In the assessment of primary aldosteronism the plasma aldosterone concentration and the plasma renin activity represent important biological markers, each of them reflecting one pathway of a counter-running biological process (Young, Endocrinol. (2003) 144: 2208-2213). The method according to the present invention may aid in the assessment of primary aldosteronism wherein the plasma aldosterone concentration is used as a first biochemical marker and the plasma renin activity as a second biochemical marker, respectively.

In a preferred embodiment of the present invention the results obtained in steps (a) and (b) as described above, are normalized to the median value of a reference population and are given as multiples of the respective median value (MOM A and MOM B). Depending on the symmetry of the distribution of (a) and (b) also the respective mean values may be suitable for normalization, instead of the medians.

The results obtained in steps (a) and (b) may be presented in the form of a vector wherein the slope of the vector (c) indicates the balance between the first and the second biochemical process. The length of the vector (d) corresponds to the overall dynamics or magnitude of the physiological condition. Preferably, the vector is derived from a calculation based on MOM-values as described above.

In a further preferred embodiment of the present invention the results obtained in steps (c) and (d) as described above are subjected to a logarithmic transformation and optionally to a coordinate shift.

The logarithmic transformation is carried out with the vector's slope (representing the balance) and the vector's length (indicating the rate of overall dynamics/turnover/magnitude). The shift of the coordinate system allows data presentation taking in account the centre of value distributions of the reference group. This procedure is based on the following considerations:

If a balance between two complementary biochemical processes is reached (c) the ratio A/B=1 with MOM A=MOM B. Thus, a logarithmic transformation would give log(1)=0. It should be noted, however, that based on actual values determined for a reference group, the mean log(c) may slightly differ from 0.

Obviously median levels of MOM A as well as MOM B equal 1 in a representative reference population. In that case the overall dynamics (d) of counter-acting parameters is calculated as the square root of $(A^2+B^2)=2^{0.5}=1.41$. Thus, a logarithmic transformation would give log(1.41)=0.15. It should be noted, however, that in practice based on values determined for a reference group, the actual average logarithm (d) may slightly differ from the theoretical value of 0.15.

Thus, for plotting log(d) versus log(c) in a further step, the coordinate system may be shifted by the mean negative log(c) and mean negative log(d) in a way to center the data on the origin of the ordinates.

It is also possible to select certain patient groups of interest. As an example in the assessment of perimenopausal osteoporosis (or of the risk to run into osteoporosis) patients may be grouped into tertiles, quartiles or quintiles for overall dynamics as well as for balance. In one embodiment cut-offs for both overall dynamics as well as for balance between formation and resorption are used. Individuals falling into the range above both the selected cut-off levels may be at higher risk to develop osteoporosis as compared to those individuals not exceeding one or both cut-off values. For certain questions in assessment of a physiological process or status it is also envisaged that different cut-off levels can be combined in order to obtain additional diagnostically relevant information.

In a still further preferred embodiment, the present invention comprises the calculation of a confidence ellipsis, e.g. 95% or 97.5% confidence ellipsis from reference data. The resulting plot consists of four fields which symbolize either dominance of A or supremacy of B, together with either high or low increments. The extent of these processes is represented by the distance from the focus of the ellipsis (the origin of ordinates).

Importantly, the method of the present invention is particularly suitable for determining the response of a subject, particularly a human subject, to a therapy, e.g. a therapy intended to increase bone formation, e.g. for the treatment of osteoporosis. The treatment of osteoporosis may involve, e.g. hormone replacement therapy, administration of bis-phosphonates, treatment with parathyroid hormone etc. The response may be assessed by determining balance and overall response of the respective physiological condition before begin of the treatment and once or several times during the course of the treatment. Preferably, the response is shown as a marker plot within a 95% confidence ellipsis.

The method of the present invention is also suitable to compare group characteristics. Groups are individuals characterized by distinct attributes, like different ranges of age, menopausal status, different stages or degree of a disease etc. These groups can be displayed relative to a reference group by using the medians of (a) and (b) of the reference group for normalization and mean log(c) and log(d) for a coordinate shift. Finally, data of each group can be visualized in form of a confidence ellipsis.

On the other hand site, different sub-groups (e.g. pre- and postmenopausal women) may be summarized within one main group (women), by using the group specific medians for normalization. This will correct e.g. for age specific fluctuations of markers, because instead of absolute values of (a) and (b), respectively, only the multiples of subgroup specific medians are used for further calculations

BRIEF DESCRIPTION OF THE DRAWINGS

Further, the present invention shall be explained in more detail by the following Figures and Examples.

FIG. 1 refers to the calculation of normalized measurement values for biomarkers.

In FIG. 2A the value for the bone formation marker, e.g. P1NP or OC is indicated on the Y-axis, preferably as a normalized MOM-value. The value of the bone resorption marker, e.g. CTX is indicated on the X-axis, preferably as a normalized value, e.g. CTX-MOM. The Y-value may be defined as formation force (F) and the X-value may be defined as resorption force (R). Different vectors resulting from different values of R and F are indicated.

The slope of the vector (F/R, i.e. ratio of bone formation to resorption force) is indicative for the balance between both processes, i.e. the balance between bone formation and resorption (as shown in FIG. 2B). Conceivably the length of the vector represents the magnitude of both complementary processes The length of the vector, which is determined (as shown in FIG. 2C) from the square root of the sum of the squared MOM's of the formation marker F and the resorption marker R, corresponds to the overall dynamics, i.e. to the overall bone turnover rate.

FIG. 3B displays the histogram of FIG. 3A in a logarithmically transformed coordinate system including a coordinate shift of −0.17 (instead the theoretical value of −0.15, see explanations above). The calculation was based on equations (c) and (d) as described in the present invention. Note the shift of "turnover" to center the data.

FIG. 4 shows a bone marker plot with 95% confidence ellipsis describing balance and turnover of bone metabolism in a set of healthy women with normal bone mineral density. Premenopausal women: filled triangles. Postmenopausal women: open triangles. The plot is calculated from CTX-OC (FIG. 4A) and CTX-P1NP (FIG. 4B). Note the overlapping of data from pre- and postmenopausal women by normalization to the respective median and an increased scattering of data derived from CTX and P1NP concentrations.

The upper left field of the graph represents dominant resorption together with high turnover, i.e. a fast bone resorption as the most unfavorable condition.

An increase or decline of bone markers is easily comprehensible from concentration data, but judging simultaneously the change in the balance between formation and resorption is elusive. The plot of balance versus rate of bone metabolism as a matter of the present intervention could be helpful in solving this dilemma.

FIG. 6 shows a comparison of group characteristics. Bone marker plots of menopausal women (MP) relative to the pre-menopausal women reference group (preMP) is shown. The medians of CTX, OC and P1NP of pre-menopausal women were used for normalization of data from postmenopausal women A): CTX and OC, B): CTX and P1NP. Note the shift toward accelerated turnover and increased bone resorption in the menopausal group (MP).

DETAILED DESCRIPTION

Examples

Example 1

Materials and Methods

Blood samples from 599 apparently healthy women (age range 25-74 years) were collected in an outpatient clinical setting during the morning. All women underwent central dual energy X-ray absorptiometry and were asked to complete a questionnaire regarding medical history and activities known to affect bone health (Kudlacek et al., Eur J Clin Invest 33 (2003), 332-339); Kudlacek et al., Eur. J. Clin. Invest. 33 (2003), 323-331). Serum samples were stored in aliquots deep frozen at −80° C. According to the WHO criteria 14 women suffered from osteoporosis due to a T-score<−2.5. In 138 individuals osteopenia was assumed by T-score≤−1 to −2.5 (Bone 27 (1994), 585-590). A normal BMD was expected by a T-score>−1 of the lumbar vertebrae 1 to 4 was found in 447 women.

The analytes β-CrossLaps (CTX), osteocalcin (OC) and N-terminal procollagen of type I collagen (P1NP) were analyzed in all samples by an Elecsys 2010 Autoanalyzer (Roche Diagnostics, Germany). To create own reference ranges samples were selected according to the criteria of a T-score≥−1, no use of glucocorticoids and normal laboratory data (calcium<2.73 μg/L, phosphate<1.6 μg/L, alkaline phosphatase<120 U/L, parathyroid hormone<60 ng/L, 25-hydroxy-vitamin D>12 μg/L and creatinine<12 mg/L).

In consistence with age, the questionnaire and analysis of follicle stimulating hormone (FSH) and 17β-estradiol (E2) concentrations we defined three sub-groups: premenopausal women (FSH<30 U/L, E2>20 ng/L; n=190), post menopausal women (FSH>30 U/L, E2<20 ng/L; n=44) and a group of perimenopausal women and women receiving a hormone replacement therapy (HRT) (FSH>30 μU/L, E2>20 ng/L; n=35).

Example 2

Calculations and Results

All calculations and graphics were done by Microsoft Excel on a personal computer. SAS for Windows 9.01 was used to prove the correctness of Excel programming for calculations of the confidence ellipsis.

The transformation procedure for concentrations of bone resorption and formation markers is explained by an example, namely the cohort of apparently healthy women with normal T-score.

2.1 Basic Characteristics and Distribution of Bone Marker Values

Bone resorption was monitored by CTX, while P1NP and OC were considered to represent bone formation. The 5%, 50% and 95% concentration values and the medians from 190 premenopausal women, 44 postmenopausal women and 35 women under HRT are given in Table 1.

TABLE 1

5/95-percentiles for the markers analyzed
The percentiles (5%/50%/95%) of a marker of bone resorption (CTX, ng/ml) and two markers of bone formation (OC and total P1NP, ng/ml, respectively) in women are shown. The respective MOM's are given in parenthesis in the line underneath the percentiles for the absolute values.

|  | CTX | OC | P1NP |
|---|---|---|---|
| Premenopausal | 0.3/0.13/0.37 | 11/21/36 | 20/36/75 |
| (n = 190) | (0.3/1/3.0) | (0.6/1/1.8) | (0.5/1/2.1) |
| Menopausal | 0.09/0.22/0.44 | 14/25/46 | 28/45/92 |
| (n = 44) | (0.4/1/2.0) | (0.5/1/1.8) | (0.6/1/2.0) |
| Peri-menopausal | 0.4/0.16/0.32 | 11/21/39 | 19/35/82 |
| and HRT (n = 35) | (0.3/1/2.0) | (0.5/1/1.8) | (0.6/1/2.3) |

TABLE 2

| | 2.5/97.5-percentiles | | |
|---|---|---|---|
|  | CTX | OC | P1NP |
| pre-MP |  |  |  |
| 2.50% | 0.03 | 11 | 19 |
| 50% | 0.13 | 21 | 36 |
| 97.50% | 0.51 | 41 | 81 |
| MP |  |  |  |
| 2.50% | 0.04 | 11 | 23 |
| 50% | 0.22 | 25 | 45 |
| 97.50% | 0.45 | 48 | 108 |
| peri-MP, HRT |  |  |  |
| 2.50% | 0.04 | 11 | 19 |
| 50% | 0.16 | 21 | 35 |
| 97.50% | 0.33 | 47 | 91 |

The 2.5 and 97.5 percentiles, respectively, are given in Table 2.

2.2 Calculation of MOM (Multiple of Median).

Individual marker concentrations are expressed as multiples of median (MOM)

$$\text{MOM}_{formation\ (CTX)} = CTX_i/\text{median}(CTX) \qquad (1)$$

$$\text{MOM}_{resorption\ (P1NP)} = P1NP_i/\text{median}(P1NP);\ \text{alternatively OC was used} \qquad (1)$$

Figure 1A:
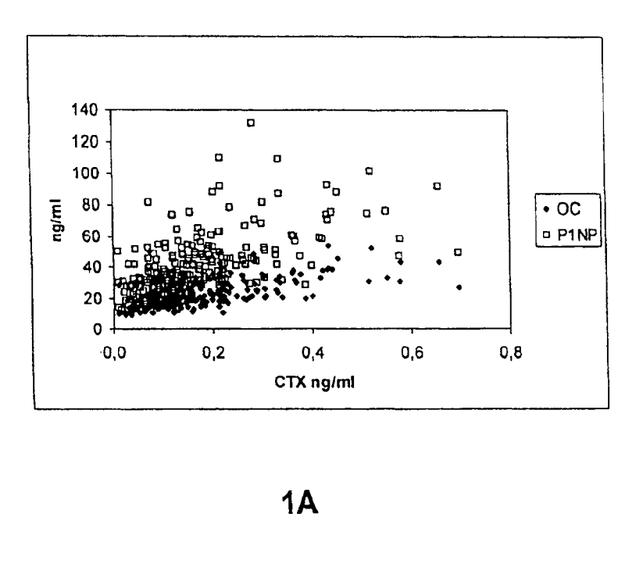
FIG. 1A is a diagram comprising non-normalized measurement values of the bone formation markers OC and P1NP (Y-axis) and for the bone resorption marker CTX (X-axis) in pre-menopausal women with normal T-score. Note the different marker concentrations.
Figure 1B:
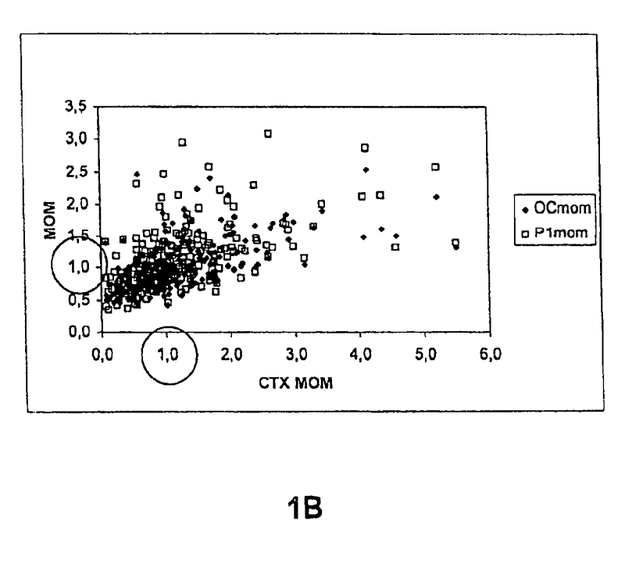
FIG. 1B refers to the calculation of normalized values for these biomarkers. The normalized values of OC, P1NP and CTX are based on the respective median values of pre- and postmenopausal women. Values are given as multiples of median value (OC-MOM, P1NP-MOM and CTX-MOM). Normalization results in a compensation of different concentration ranges. The data concentration around MOM=1 is evident.

MOM represents the distance of an observation from the central level of a group of observations. Thus MOM equalizes the different concentration scales of the bone markers (FIG. 1). Additionally, the sub-groups of perimenopausal and postmenopausal women could be matched by dividing the data by the respective medians.

2.3 Assessment of Balance and Rate of Bone Turnover by Combination of MOM's from Formation and Resorption Markers.

Figure 2:
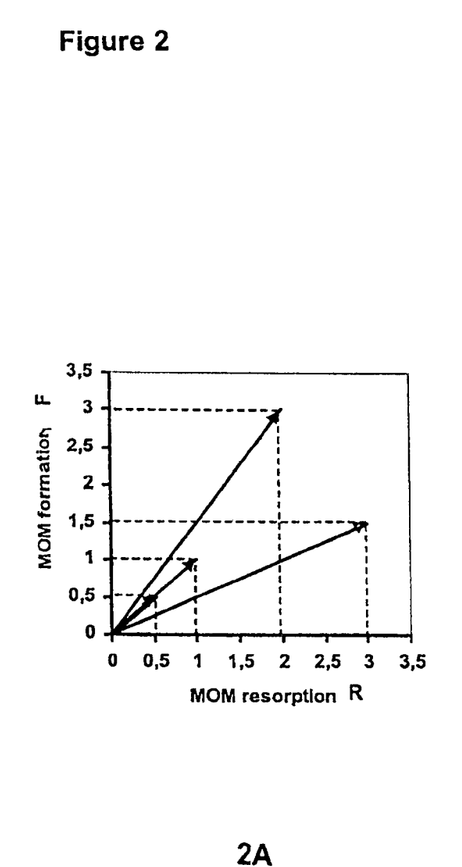
FIG. 2 shows the principle for the assessment of the balance and the overall dynamics/magnitude of a physiological condition by determining a first biochemical marker (e.g. bone formation marker=F) and a second biochemical marker (e.g. bone resorption marker=R).

MOM of markers are used as surrogate representing the "forces" of formation and resorption, which are operative on the bone and give rise to a vector as shown by the examples in FIG. 2. The slope of the vector represents the balance (ratio) between the forces of formation and resorption (2):

$$\text{Balance(vector's slope)} = \text{MOM}_{formation\ (P1NP)}/\text{MOM}_{resorption\ (CTX)} \qquad (2)$$

With equal forces of formation and resorption, the slope will be 1. If the MOM of formation predominates, the slope is >1. A slope <1 results from preponderant resorption.

Low MOM's represent "silent" bones, while high marker levels (MOM>>1) commonly are interpreted to represent a high bone turnover (Garnero et al. (1999), supra; Srivastava et al. (2005), supra). Thus the length of the vector represents the bone turnover rate. It is calculated according to the sentence of Pythagoras (3):

$$\text{Turnover rate(vector's length)} = \text{square root } (\text{MOM}_{formation\,(P1NP)}{}^{\wedge}2 + \text{MOM}_{resorption\,(CTX)}{}^{\wedge}2) \quad (3)$$

2.4 Logarithmic Transformation and Shift of the Cartesian Coordinates.

Figures 3, 3A:
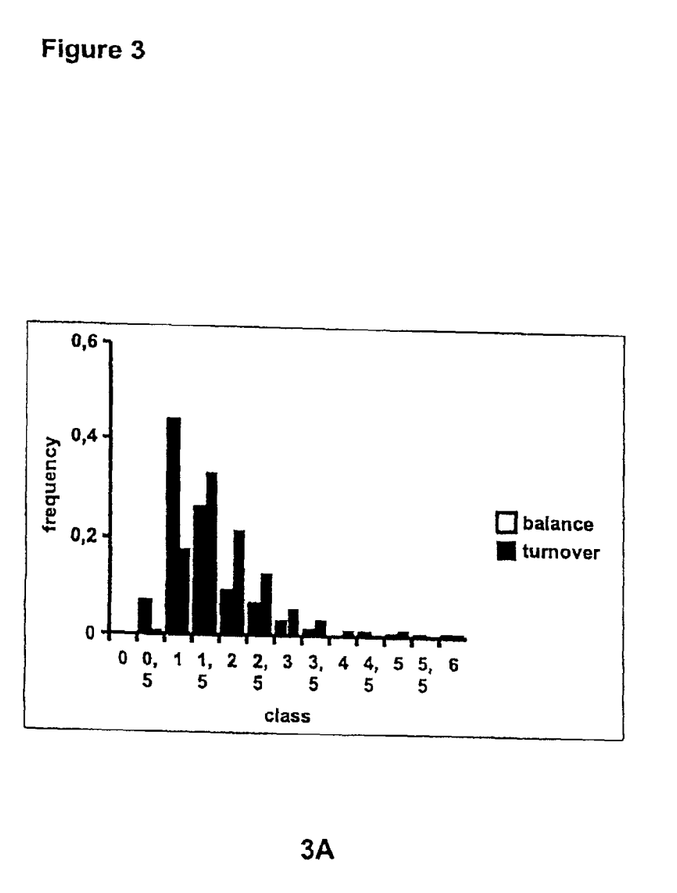
FIG. 3 shows the principles underlying the log transformation and coordinate shift.
In FIG. 3A the frequency-distribution of MOM-normalized balance of bone formation and turnover in premenopausal women is shown (linear scale).

It appeared from histograms, that the calculated balance and rate of turnover are left-handed skewed (FIG. 3A, 3B). By a log-transformation the distributions of results became more symmetrically. Assuming that $\text{MOM}_{P1NP}=1$ and $\text{MOM}_{CTX}=1$ (both values equal to the central levels of formation and resorption markers, respectively), it follows from equation (2) log(1/1)=0 and from equation (3) log(root(1+1))= 0.15. In our example of reference women the mean of log(balance) was 0.01 and 0.02 for OC-CTX and P1NP-CTX respectively. The mean of log(rate) was 0.17 and 0.18 for OC-CTX and P1NP-CTX. Thus the real numbers are close to the theoretical values. By subtraction of these mean levels from each log(balance) and log(rate) value, a shift of the coordinates is achieved (4). Thus the centre of data equals the origin (x=0, y=0).

$$x = \log(\text{balance})_i - \text{mean}(\log(\text{balance}))_{1\,to\,n}$$

$$y = \log(\text{rate})_i - \text{mean}(\log(\text{rate}))_{1\,to\,n} \quad (4)$$

2.5 Presentation of the Reference Group Data by 95% Confidence Ellipsis

The calculation of the 95% confidence ellipsis is described as follows:

Equations for calculation of confidence ellipses were adapted from Landtwing. Airborne Laser Scanning. Diploma Thesis, Swiss Federal Institute of Technology Zurich (2005), p. 24-26; Schwarze et al. ArcView-extension VISAR-Visualisierung von Aktionsräumen. Progress Report Traffic and Spatial Planning 95, Institute for Traffic Planning and Transportation Research, Swiss Federal Institute of Technology Zurich (2001), p. 6-7.

1.) List of Abbreviations:
Sxx, Syy, Sxy, Syx covariances
X mean x: balance, as calculated from (1), (2) and (4)
Y mean y: turnover rate, as calculated from (1), (3) and (4)
n number of paired observations
f sigma (f=2.5 for 95% confidence)
α large axis of ellipsis
β small axis of ellipsis
A slope of the regression line for balance (x) versus rate (y)
w radiant (ambiguous)
W definitive radiant, represents the angle of the large axis α
$E_i$ radiant for the construction point to point of ellipsis (0° to 360° in 10° steps)

2.) Matrix and Definitions of Covariances:

$$S = \begin{matrix} Sxx & Syy \\ Sxy & Syx \end{matrix}$$

$$Sxx = \text{sum}[(x-X) \wedge 2]/(n-2) \quad [a]$$

$$Syy = \text{sum}[(y-Y) \wedge 2]/(n-2) \quad [b]$$

$$Sxy = Syx = \text{sum}[(x-X)*(y-Y)]/(n-2) \quad [c]$$

3.) Equations for Calculation of 95% Confidence Ellipsis $$\alpha = f*\text{root}\{[(Sxx+Syy)/2) + \text{root}((Sxx-Syy)/2)^{\wedge}2 + Sxy^{\wedge}2)]\} \quad [d]$$

$$\beta = f*\text{root}\{[(Sxx+Syy)/2) - \text{root}((Sxx-Syy)/2)^{\wedge}2 + Sxy^{\wedge}2)]\} \quad [e]$$

$$w = \arctan[2*Sxy/(Sxx-Syy)]/2 \quad [f]$$

The result of equation [f] is ambiguously, according to sign and size of the radiant of arc tan different angles are possible. By testing the signs of A and w the definitive radiant W is obtained by equation [g]:

$$W = \text{if}(\text{and}(0<A; 0<w); w; \text{if}(\text{and}(0>A; 0<w); \pi/2+w; \text{if}(\text{and}(0<A; 0>w); \pi/2+w); w))) \quad [g]$$

4.) Point to Point Construction of the Ellipsis:

An ellipsis with the axis α and β is constructed point to point by calculation of $x_i'$ and $y_i'$ using the radiant $E_i$ (i=10° steps form 0° to 360°)

$$x_i' = \alpha*\sin(E_i) \text{ and}$$

$$y_i' = \beta*\cos(E_i) \quad [h]$$

The centre of this ellipsis is the origin (0/0) and the angle of its large axis is zero. The definitive radiant W and a shift of the centre by X and Y is considered by a transformation of the coordinates by W, X and Y:

$$x = X + x'*\cos(W) - y'*\sin(W) \text{ and}$$

$$y = Y + x'*\sin(W) + y'*\cos(W) \quad [i]$$

It is based on the covariance-matrix of data, a logic test to select the appropriate solution of the arc tan function and is build up by point to point construction. The SAS Program yielded identical ellipses (not shown).

2.6 Four Field Bone Marker Plot

Figures 4, 4A:
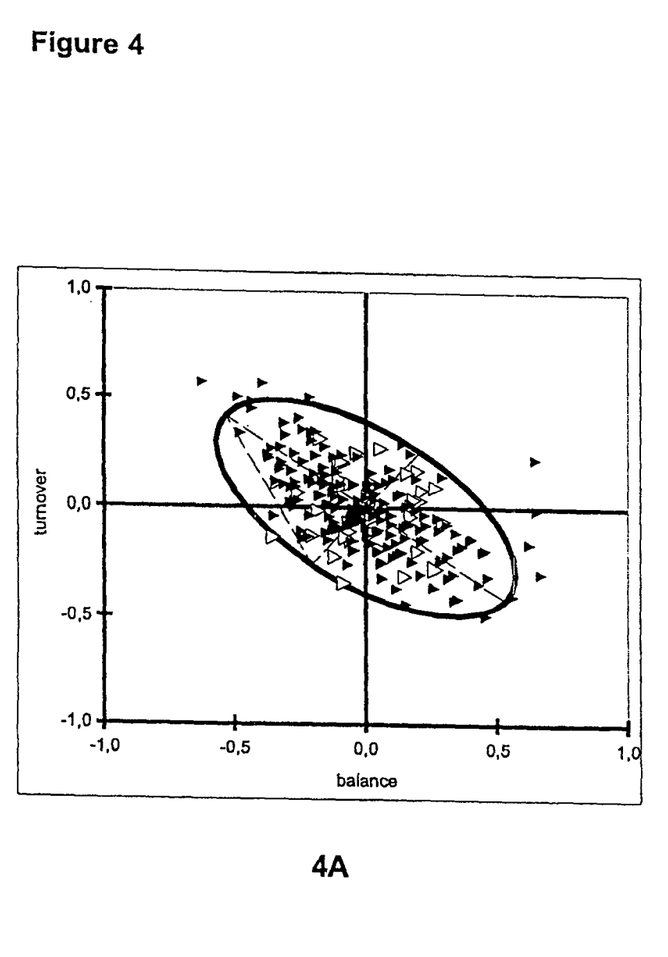
Figure 4B:
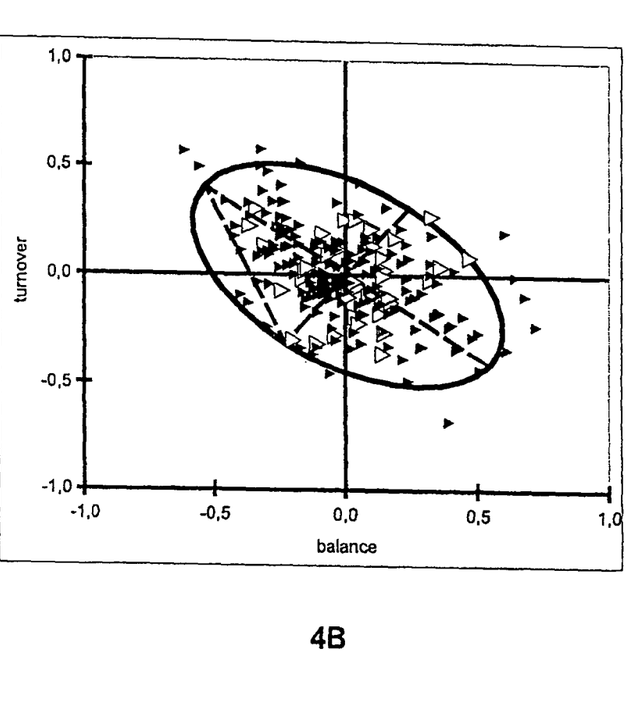

Logarithms of balance and rate of bone turnover, obtained from conjoint concentrations of bone formation and resorption markers, were plotted. The 95% confidence ellipsis is shown as well (FIG. 4A, 4B). The upper left field of the graph represents dominant resorption together with high turnover, i.e. a fast bone resorption as the most unfavorable condition. The left bottom field symbolizes slow resorption. The right hand site represents favorable settings, since the right bottom field corresponds to slow formation and the upper right field typifies fast bone formation. Not surprisingly, there are slight differences in confidence ellipses based on either OC-CTX or P1NP-CTX.

TABLE 3

Distribution of features
The distribution of the features "fast resorption" (FR), "fast formation" (FF), "slow formation" (SF), "slow resorption" (SR) was related to four fields of the plot.

| CTX-OC: | | | | CTX-P1NP: | | | |
|---|---|---|---|---|---|---|---|
| FR | FF | SF | SR | FR | FF | SF | SR |
| 33% | 15% | 33% | 19% | 32% | 16% | 30% | 23% |

As evident from the above data, approximately a ⅓ of women were allocated either to the left upper or right bottom fields, respectively, and about ⅙ was assigned to the right upper and left bottom fields, respectively.

Figure 5:
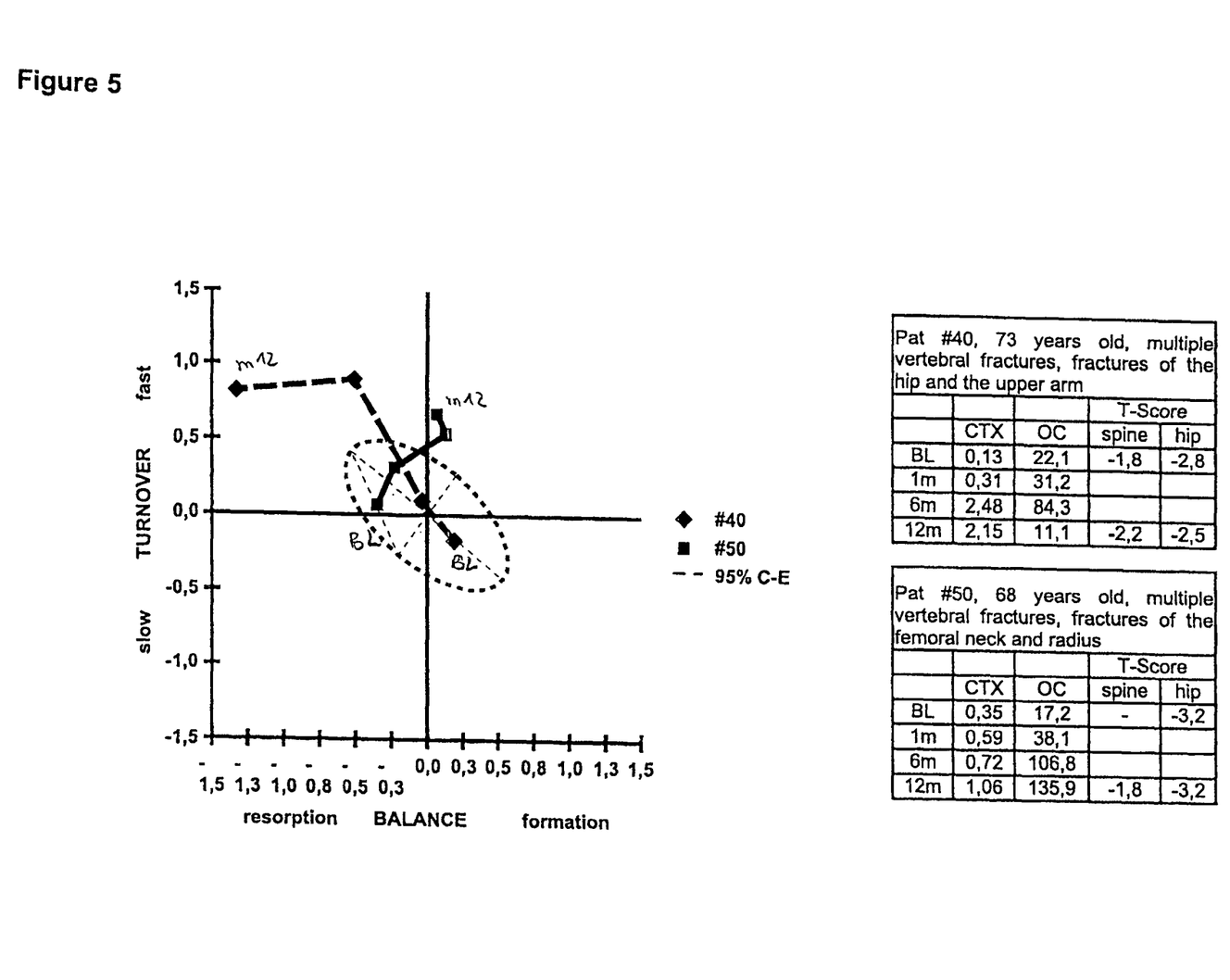
FIG. 5 shows bone marker plots from therapy monitoring of 2 patients receiving the PTH-analog Forsteo®. At baseline and at 1, 6 and 12 months CTX and OC were measured (see BL and m12). According to the marker behavior one patient may gain profit from the treatment. The other patient similarly presented with an increase in turnover rate within one month, but drifted to excessive resorption during the follow-up.

The concentrations of bone formation and resorption markers are shown in Table 4 from a follow-up of two menopausal women treated by Forsteo® within one year. In both women CTX and OC increased from baseline up to half a year. These data were transformed exactly in the same way as described for the reference group. Forsteo® increased bone turnover in both women at least within one month. According to the markers patient #50 may have gained profit by a shift from dominant bone resorption toward bone formation after one year treatment. In patient #40 a flop was observed due to the outcome of an accelerated bone resorption (FIG. 5).

TABLE 4

Patient characteristics
CTX (reference range 0.09-0.44 ng/ml) and OC (reference range: 14-46 ng/ml) were measured at baseline and at 1, 6 and 12 during of therapy with forsteo ® (BL, 1 m, 6 m, 12 m). T scores were determined at baseline (BL) and 12 months.

| | Pat #40, 73 years old, multiple vertebral fractures, fractures of the hip and the upper arm | | | | Pat #50, 68 years old, multiple vertebral fractures, fractures of the femoral neck and radius | | | |
|---|---|---|---|---|---|---|---|---|
| | | | T-Score | | | | T-Score | |
| | CTX | OC | spine | hip | CTX | OC | spine | hip |
| BL | 0.13 | 22.1 | −1.8 | −2.8 | BL 0.35 | 17.2 | — | −3.2 |
| 1 m | 0.31 | 31.2 | | | 1 m 0.59 | 38.1 | | |
| 6 m | 2.48 | 84.3 | | | 6 m 0.72 | 106.8 | | |
| 12 m | 2.15 | 11.1 | −2.2 | −2.5 | 12 m 1.06 | 135.9 | −1.8 | −3.2 |

Figures 6, 6A:
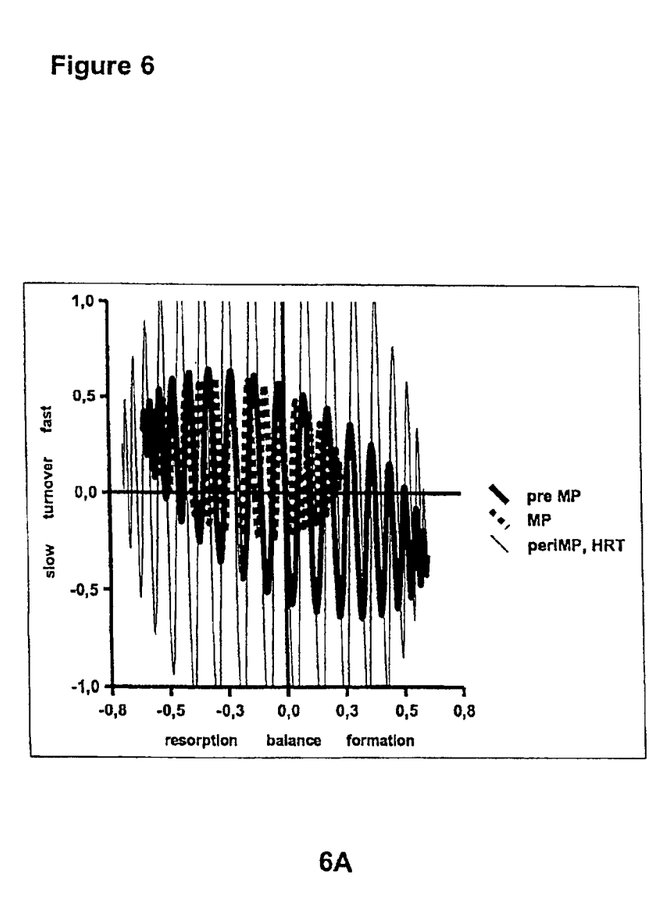
Figure 6B:
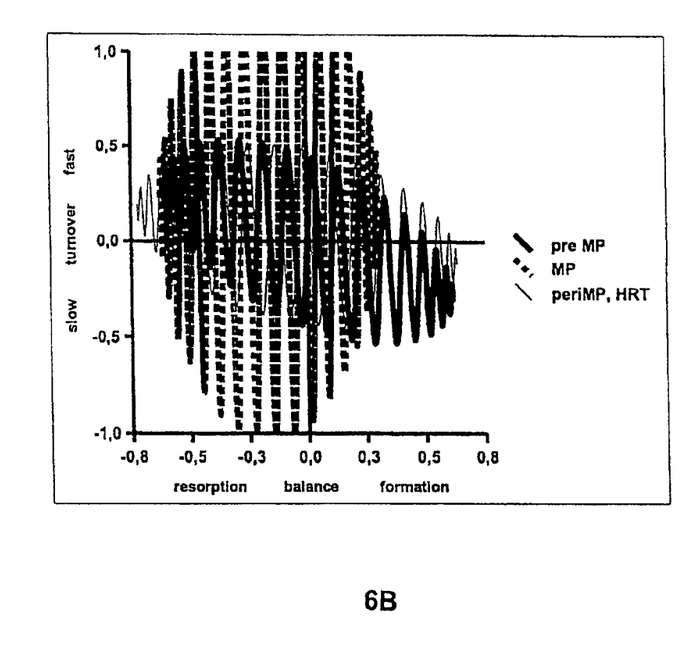

A different type of evaluation is shown in FIG. 6. Only the median of premenopausal women was used for MOM-normalization. The groups of pre- peri- and postmenopausal women are presented by distinct confidence ellipsis to circumscribe the group characteristics. The accelerated bone resorption in menopausal women is visualized by a shift of the ellipsis toward the left upper field. The ellipsis for perimenopausal women (including females under hormone replacement) was similar to that of premenopausal woman. Basic characteristics as well as abnormalities of bone metabolism, which is a prototype of a counter-acting and balanced physiological process, can be easily spotted by applying the method as described herein above. For assessment of osteoporosis different cut-offs may be chosen, as required. The group of individuals presenting with both elevated dynamics and an impaired balance (increased resorption) is likely to be in need of further investigations and/or an anti-osteoporotic therapy.

The invention claimed is:

1. A method for assessing in vitro a balance and an overall dynamic of bone metabolism wherein balance refers to a status of bone metabolism as a result of two complementary and/or counter-acting biochemical processes, and overall dynamic refers to a magnitude of the status of bone metabolism, the method comprising:

a) measuring a first biochemical marker representing a first biochemical process associated with bone metabolism to yield a result;
   b) measuring a second biochemical marker representing a second biochemical process associated with bone metabolism to yield a result, wherein measurements obtained from a) and b) are presented in the form of a vector;
   c) calculating a ratio of the results obtained in (a) and (b) to yield a slope of the vector;
   d) calculating a square value of the result from (a) and a square value of the result from (b), adding the square values to yield a sum, and calculating the square root of the sum to yield a length of the vector;

wherein the ratio calculated in (c) is used to assess the balance of bone metabolism and wherein the square root calculated in (d) is used to assess the overall dynamic of bone metabolism.

2. The method of claim 1, wherein said first biochemical marker is a marker of bone formation.

3. The method of claim 2, wherein said marker of bone formation is selected from the group consisting of bone alkaline phosphatase, osteocalcin (OC), and procollagen 1 N-terminal propeptide (P1NP).

4. The method of claim 1, wherein said second marker is a marker of bone resorption.

5. The method of claim 4, wherein said marker of bone resorption is a selected from the group consisting of a cross-linked telopeptide of type I collagen, and tartrate-resistant acidic phosphatase.

6. The method of claim 1, further comprising normalizing the results obtained in steps (a) and (b) to a mean value of a control group and providing the normalized results as multiples of said mean.

7. The method of claim 1 further comprising subjecting the results obtained in steps (a) and (b) to a logarithmic transformation and optionally to a coordinate shift.

8. The method of claim 1 further comprising calculating a confidence ellipse from the results obtained in steps (a) and (b).

9. A method for comparing group characteristics of subjects, the method comprising: providing a reference group and assessing each member of the reference group according to the method of claim 1; calculating medians of the results of (a) and (b); and normalizing with the calculated medians; calculating a mean log (c) and a mean log (d) for a coordinate shift.

10. The method of claim 5, wherein said marker of bone resorption is a cross-linked telopeptide of type I collagen selected from the group consisting of cross-linked N-telopeptide (NTX), cross-linked C-telopeptide (CTX) and type 1 collagen carboxyterminal telopeptide-1 (ICTP).

* * * * *